United States Patent
Auta et al.

(10) Patent No.: US 6,964,958 B2
(45) Date of Patent: Nov. 15, 2005

(54) METHOD OF SIMULTANEOUSLY TREATING SENSORY AUDITORY GATING DEFICIT AND ASSOCIATED PSYCHOSIS IN SCHIZOPHRENIA AND BIPOLAR DISORDER PATIENTS WITH MANIA

(76) Inventors: James Auta, 2314 W. Flournoy St., Chicago, IL (US) 60612; Erminio Costa, 333 E. Ontario (#3302b), Chicago, IL (US) 60611; John M. Davis, 442 Webster Ave., Chicago, IL (US) 60614; Alessandro Guidotti, 859 N. Dearborn, Chicago, IL (US) 60610; Patricia Tueting, 488 Ash St., Winnetka, IL (US) 60693

( * ) Notice: Subject to any disclaimer, the term of this patent is extended or adjusted under 35 U.S.C. 154(b) by 0 days.

(21) Appl. No.: 10/252,030

(22) Filed: Sep. 20, 2002

(65) Prior Publication Data

US 2003/0119821 A1 Jun. 26, 2003

Related U.S. Application Data

(60) Provisional application No. 60/325,672, filed on Sep. 28, 2001.

(51) Int. Cl.$^7$ .............................................. A61K 31/55
(52) U.S. Cl. ...................... 514/220; 514/962; 424/451; 424/464
(58) Field of Search ................................ 514/220, 962; 424/451, 464

(56) References Cited

U.S. PATENT DOCUMENTS

| | | | | |
|---|---|---|---|---|
| 4,180,668 A | * | 12/1979 | Hester, Jr. | .................... 540/566 |
| 5,317,018 A | * | 5/1994 | Walser et al. | ................ 514/220 |
| 6,528,649 B2 | * | 3/2003 | Cai et al. | ...................... 546/84 |

FOREIGN PATENT DOCUMENTS

EP   0 573 982   12/1993

* cited by examiner

*Primary Examiner*—Frederick Krass
(74) *Attorney, Agent, or Firm*—Ladas and Parry LLP

(57) ABSTRACT

Schizophrenia and bipolar disorders with mania may be treated by imidazenil or other benzodiazepine-3-carboxamide derviatives.

5 Claims, 6 Drawing Sheets

Fig. 1. Pharmacological profiles if imidazenil (a partial positive-allosteric modulator) and alprazolam (a full positive-allosteric modulator). Abscissa: ED$_{50}$ for imidazenil and alprazolam. Ordinate: behavioral tests predicting side effects (1, 2, 3) or clinically useful (4) sedative, (5) anxiolytic, (6, 7) anticonvulsant, and (8) antipanic activity. For details, see Costa et al. (2001)

Fig.2. Diagram of GABA$_A$ receptor showing sites of action of the various classes of anti-epileptic drug (from Meldrum and Whiting, 2001)

Alprazolam fails to modify prepulse inhibition of startle in heterozygous reeler mouse (HRM)

t-test: **<0.01, p<0.05(paired; #p<0.01(independent groups):

Table 1. Proposed roles of $GABA_A$-receptor subtypes in benzodiazepine actions

|  | $\alpha_1$ | $\alpha_2$ | $\alpha_3$ | $\alpha_5$ |
|---|---|---|---|---|
| Sedation | + | − |  | − |
| Amnesia | + | − |  |  |
| Seizure protection | + | + |  |  |
| Anxiolysis | − | + |  |  |

From Möhler 1999, 2001 (modified)

FIGURE 5

Table 2 Summary of anatomical abnormalities in the brains of schizophrenic patients and the heterozygote reeler mouse

| Schizophrenia Patients | Heterozygote Reeler Mouse |
|---|---|
| ↑ Dilation of Lateral Cerebral Ventricles (Johnstone et al 1976; Weinberger et al 1993) | (not yet quantified) |
| ↑ Cell Packing Density in Frontal Cortex (Selemon & Goldman-Rakic 1999) | ↑ Cortical Neuronal Packing Density (Liu et al., 2001) |
| ↓ Neuropil Density in Frontal Cortex (Selemon & Goldman-Rakic 1999) | ↓ Cortical Neuropil Density (Liu et al., 2001) |
| ↓ Dendritic Spine Density on Layer III Pyramidal Cells (Glantz & Lewis 2000) | ↓ Dendritic Spine Density on Layer III Pyramidal Cells (Liu et al., 2001) |
| Altered Distribution of NADPH-diaphorase Positive Cells (Akbarian et al 1993) | Altered Distribution of NADPH-Diaphorase Cells (Tueting et al., 1999) |
| ↓ $GAD_{67}$ mRNA and Protein in Frontal Cortex (Impagnatiello et al 1998; Guidotti et al 2000) | ↓ $GAD_{67}$ mRNA and Protein Levels (Liu et al., 2001) |
| ↓ $GAD_{67}$ mRNA Positive Cells in Frontal Cortex (Akbarian et al 1995; Volk et al 2000) | ↓ Number of $GAD_{67}$-Positive Cells in Frontal Cortex (Liu et al., 2001) |
| ↓ Reelin mRNA and Protein in Frontal Cortex (Impagnatiello et al 1998; Guidotti et al., 2000) | ↓ Reelin Protein and mRNA Levels (Tueting et al., 1999; Liu et al., 2001) |
| ↓ Number of Reelin-Positive Cells (Impagnatiello et al 1998; Guidotti et al., 2000) | ↓ Number of Reelin-Positive Cells (Liu et al., 2001) |
| Disruption of Physiological Correlation between Reelin and $GAD_{67}$ (Guidotti et al, 2000) | Loss of Correlation between Reelin and $GAD_{67}$ Levels (Carboni et al., 2000) |

FIGURE 6

METHOD OF SIMULTANEOUSLY TREATING SENSORY AUDITORY GATING DEFICIT AND ASSOCIATED PSYCHOSIS IN SCHIZOPHRENIA AND BIPOLAR DISORDER PATIENTS WITH MANIA

Priority is claimed from U.S. Provisional patent application 60/325,672 filed Sep. 28, 2001.

FIELD OF THE INVENTION

The present invention relates to the treatment of patients suffering from schizophrenia and patients suffering from bipolar disorders with mania.

BACKGROUND OF THE INVENTION

GABAergic inhibition is increasingly considered one of the most important factors in controlling the mode of operation of thalamo-cortical and re-entrant cortico-thalamic pathways as well as of the afferent septal-hippocampus and of the re-entrant hippocampal-septal glutamatergic pathways that are substrates for the regulation of complex brain functions, including normal sensory, gating, cognition, vigilance, spatial orientation, volition, and consciousness. These functions are altered in schizophrenia and bipolar disorder patients with mania. Thus, one may attribute the appearance of psychotic symptoms in these mental disorders to a deficit in GABAergic modulation in critical cortico-thalamic and cortico-hippocampal brain circuits.

Indeed, schizophrenia and bipolar disorder patients with mania who manifest an auditory gating deficit and who suffer from other associated problems, such as auditory hallucinations, cognitive impairment, delusions, and defects of volition (lack of motivation, flat affect, and social withdrawal), express downregulation of GABAergic synthesis and function in their cortical, thalamic, septal, and hippocampal circuits (Guidotti et al., 2000). The neuroanatomical and neurochemical abnormalities of the GABAergic system in postmortem brain of patients with schizophrenia and bipolar disorder with mania can be summarized as follows: 1) decreased GABA release and uptake (Reynolds et al., 1990; Sherman et al., 1991; Simpson et al., 1998); 2) increased denervation-dependent $GABA_A$ receptor density measured by $^3H$-muscimol binding, particularly in layer II of the prefrontal cortex (PFC) and in superficial layers of other adjacent cortical areas (Benes et al., 1992; Benes, 2000); 3) increased expression of the $\alpha1$ $GABA_A$ receptor subunit mRNA in the PFC (Impagnatiello et al., 1998); 4) a dorsolateral PFC decrease of presynaptic GABA transporter-1-positive cartridges in GABAergic axon terminals of chandelier cells impinging on the initial segments of pyramidal axons (Woo et al., 1998), and decreased $GAD_{67}$ expression (this enzyme is important in the synthesis of GABA and is one of the two molecular forms of glutamic acid decarboxylase expressed in GABAergic neurons, the other being $GAD_{65}$) (Akbarian et al., 1995; Impagnatiello et al., 1998; Benes 2000; Bunney and Bunney, 2000; Guidotti et al., 2000; Volk et al., 2000), which taken together suggest that GABAergic function may be downregulated; and 5) an altered cortical distribution of nicotinamide adenine dinucleotide phosphate-positive GABAergic cells (Akbarian et al., 1996).

Collectively, these data support the hypothesis that GABAergic downregulation in cortical and hippocampal networks involved in sensory information processing act as a vulnerability factor in the etiopathogenesis of psychosis and may contribute to sensory gating deficits and to the presence of visual and auditory hallucinations, cognitive impairment, and social withdrawal. As a general strategy, our studies are directed at testing whether drugs that tend to normalize a deficient GABAergic system may also be beneficial in correcting the deficit of auditory gating in schizophrenia. This deficit, commonly known as a defective prepulse inhibition of startle (PPI) is considered the most important among the few objective measurements of brain neuronal network functional alterations that can be measured in patients with psychotic disorders and in their relatives (Swerdlow & Geyer, 1998).

New therapeutic opportunities arise today due to increasing insights into the molecular architecture and diversity of components involved in signal transduction at $GABA_A$ receptors (FIG. 2). Based on the brain expression of seven subunit families comprising at least 18 different subunits ($\alpha1$–6, $\beta1$–3, $\delta$, $\epsilon$, $\theta$, $\rho1$–3) that are assembled in heteropentameric $GABA_A$ receptors, an extraordinary structural heterogeneity of the target for GABA is operative in the CNS (Barnard, 2001). Most $GABA_A$ receptor subtypes in brain are believed to be composed of $\alpha\beta\gamma$ subunits associated to form the above-mentioned heteropentameric structures termed $GABA_A$ receptors (FIG. 2). Although the physiological significance of this heterogeneity is only partially understood, the pharmacological significance of the various subunits with respect to, their association with various actions of anxiolytic benzodiazepines and congeners is beginning to be quite well understood. For example, $GABA_A$ receptors containing $\alpha$ and $\gamma$ subunits are substrates for a wide spectrum of actions elicited by clinically available agonists acting at the modulatory benzodiazepine binding sites. These sites are located at the interface of the postsynaptic ectodomains of contiguous $\alpha$ and $\gamma$ subunits on $GABA_A$ receptors composed of $\alpha\beta\gamma$ subunits (FIG. 2). Benzodiazepine—sensitive $GABA_A$ receptors are characterized by the expression of $\alpha_1$, $\alpha_2$ $\alpha_3$ or $\alpha_5$ subunits in their heteropentameric structure and by the contiguity of these $\alpha$ subunits with $\gamma_2$ subunits. The GABA-gated ion channel opening frequency of these receptors is promptly enhanced to maximal efficacy by agonists of benzodiazepine sites currently available on the US market and this is the basis for their therapeutic effectiveness in the treatment of anxiety disorders, sleep disturbances, muscle spasms, and epilepsy. However, maximal amplification of GABA-gated channels by benzodiazepines is also the basis of undesirable side effects, such as sedation, amnesia, tolerance, and dependence (Costa and Guidotti, 1996).

In present clinical practice the consensus is that in schizophrenia protracted benzodiazepine monotherapy is not effective, despite anecdotical reports of antipsychotic efficacy in the first few days of treatment. The lack of antipsychotic action after protracted benzodiazepine treatment is presumably attributable to the well known phenomenon of tolerance that inevitably and rapidly occurs after administration of clinically-available benzodiazepine. Moreover their use is generally contraindicated because dlinically-available benzodiazepine drugs also elicit sedation and amnesia, and if used repeatedly in addition to tolerance produce dependence (Costa et al., 2001).

Recent studies (Möhler, 2001) have established that the sedative and amnestic action of benzodiazepines is related to the amplification of GABA action at $GABA_A$ $\alpha_1$ receptors including $\alpha_1$ subunits contiguous to the $\gamma_2$ subunits, whereas their anxiolytic and anticonvulsant and antipsychotic actions are mediated presumably by similar actions at $GABA_A$ receptors having $\alpha_2$, $\alpha_3$ or $\alpha_5$ receptor subunits (Table 1).

Thus, opportunities for the design of a new generation of benzodiazepine binding site ligands that are partial agonists and act specifically at $GABA_A$ receptor subtypes, are now emerging. These new drugs have reduced tolerance and dependence liability and selectively act on $GABA_A$ receptor subtypes to control psychotic symptoms in schizophrenia patients without sedative or amnestic action.

U.S. Pat. No. 5,317,018 of May 31, 1994 describes the use of imidazo[1,5-a]benzodiazepine-3carboxamide derivatives and compositions containing such compounds for treating anxiety and panic disorders and idiopathic and psychomotor epilepsy. One such compound is 6-(2 bromophenyl)-8-fluoro-4H-imidazo[1,5a][1,4]benzodiazepine-3-carboxamide which is often referred to as imidazenil.

Unlike other partial allosteric modulators, imidazenil has a high affinity for the receptor, does not act on $GABA_A$ $\alpha_1$ subunit and is slowly metabolized in compounds that may act on $GABA_A$ $\alpha_1$ subunit. Thus, imidazenil does not produce sedation and does not produce tolerance or dependence as indeed occurs with other partial allosteric modulators of the action of GABA at $GABA_A$ receptors (Costa et al. 2001).

Auta et al PNAS 97 (No.5) 2314–2319 (Feb. 29, 2000) describe the use of imidazenil to prevent alprazolam-induced aquisition in patas monkeys and note that during a seventeen day treatment no tolerance of the effects of imidazenil were noted. Costa et al TiPS May 1996, 192–200 suggest that imidazenil may be a prototype of a new generation of anxiolytic and anticonvulsant drugs that have minimal disruptive effects on learning and memory, and are virtually devoid of the tolerance liability and other unwanted side-effects of classic benzodiazepines. As a reference compound, we used the clinically available benzodiazepine alprazolam, an 8chloro-1-methyl-6-phenyl-4-[1,2,4]triazolo[4,3a][1-4]benzodiazepine whose formula is also indicated in FIG. 1.

SUMMARY OF THE INVENTION

The present invention provides a method of treatment of patients suffering from schizophrenia or bipolar disorder with mania which comprises administering to them a therapeutically effective amount of a compound of the formula:

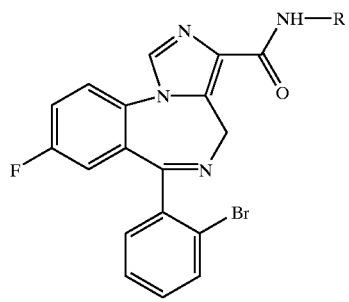

wherein R is selected from hydrogen, $CH_3CH_2$—, $CH_2$=$CHCH_2$—, $(CH_3)_2CH$—, $CH_3CH_2CH_2$— or

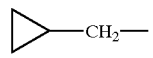

or a pharmaceutically acceptable salt thereof.

BRIEF DESCRIPTION OF THE DRAWINGS

FIG. 5 is a Table showing the possible roles of $GABA_A$—recptor subtypes in benzodiazepine actions.

FIG. 6 is a Table summarizing anatomical abnormalities in prefrontal cortex of schizophrenic patients and heterozygous reeler mice.

DETAILED DESCRIPTION OF THE INVENTION

The compounds for use in the present invention are described in U.S. Pat. No. 5,317,018 which, as noted above, describes their anti-anxiety and anti-epileptic properties. In view of the general view that benzodiazepines are not useful in the treatment of schizophrenia or bipolar disorders with mania, however, it is surprising that these can find use in treatment of these conditions. Therefore our invention and the reasoning underlying it presents a novel approach to the treatments in these diseases.

A preferred compound for use in the present invention is imidazenil which is a compound of the above formula wherein R is hydrogen.

Suitable pharmaceutically acceptable salts include salts with hydrochloric acid, hydrobromic acid, nitric acid, sulfuric acid, phosphoric acid, methanesulfonic acid, paratoluenesulfonic acid and other acids conventionally used for this purpose.

The choice of a therapeutically effective dose will be made by a physician and vary depending on the compound used and the precise condition of the patient. The determination of a suitable dose for a given patient can be made by conventional means for selecting doses of compounds for treatment of the condition in question. For example determination of a suitable dose may be effected by the degree of anxiety or by preexisting susceptibility to seizures. Guidance as to the ways to determine suitable doses for treatment of schizophrenia and bipolar disorders with mania may be found in articles by Costa et al 2001.

Typical doses are likely to be in the range of $\mu$g/kg, for example from 1 to 10 $\mu$g/kg. Doses will typically be taken 1–2 times per day. Suitable dosage units will contain from 0.05 to 0.5 mg of active compound.

The compounds will be administered orally and will be formulated as pills or capsules. Such pills or capsules may contain from 0.05 to 0.5 mg of the inventive compound, and the remaining weight balance comprising a pharmaceutically acceptable carrier.

Figure 1:
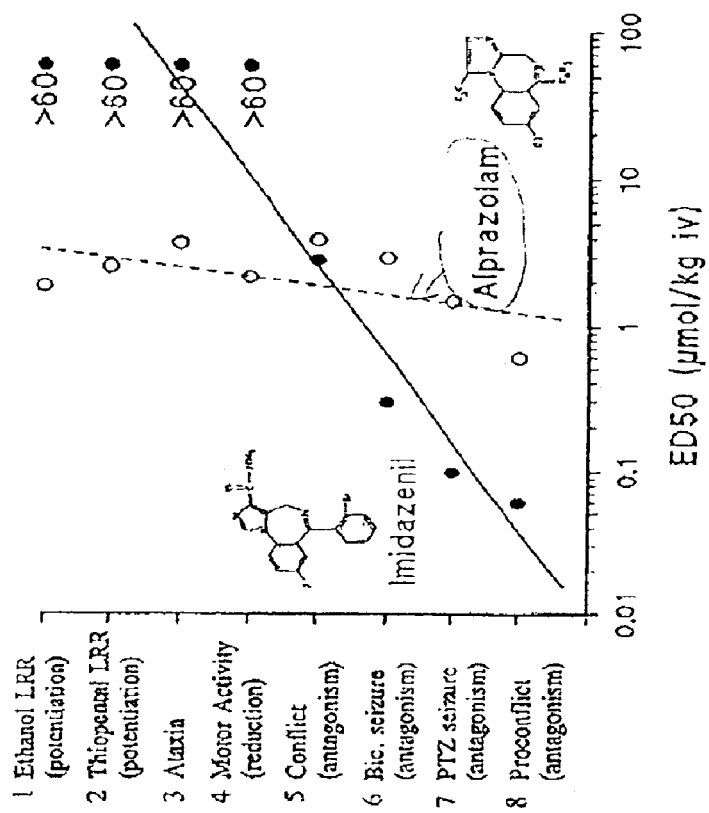
FIG. 1 is a graph comparing the pharmacological profiles of imidazenil and a classical benzodiazepine, alprazolam.
Figure 2:
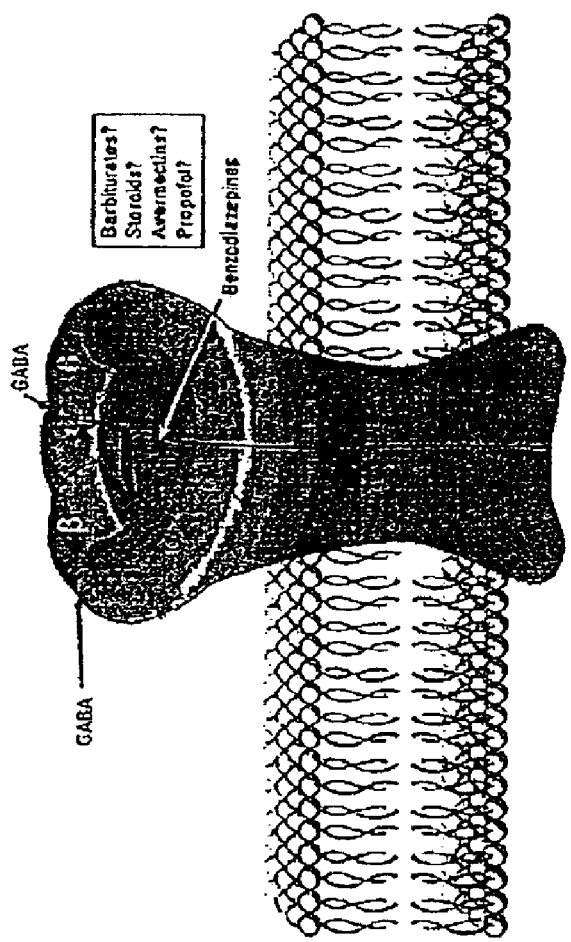
FIG. 2 is a diagram of a $GABA_A$ receptor.

FIG. 1 compares the dose-response actions of alprazolam (a classic clinically utilized benzodiazepine ligand) with that of imidazenil (which is the inventive compound). An important aspect of the pharmacological profile of imidazenil that distinguishes this drug from alprazolam or other classic benzodiazepines is its ability to elicit potent anticonvulsant and anxiolytic pharmacological effects at doses that are several orders of magnitude smaller than doses eliciting sedation or amnesia (FIG. 1, Costa et al., 2001). In fact, imidazenil, in doses up to 60-fold greater than doses producing anxiolytic and anticonvulsant actions antagonizes the sedative and amnestic actions of alprazolam in rats and monkeys without causing tolerance (Auta et al., 2000; Costa et al., 2001). A pharmacological profile similar to that of imidazenil is observed for its derivatives as reported in Table 1 of U.S. Pat. No. 5,371,018. Imidazenil has been reported to have a high affinity for benzodiazepines binding sites and a low clearance rate (in rats, T ½90 min; in nonhuman primates T ½ longer than 6 hr) and to act as a partial agonist in at least eight subtypes of $GABA_A$ receptors in which it has been tested (Costa and Guidotti, 1996). Imidazenil never maximizes the intensity of GABA-gated $Cl^-$ currents and is virtually devoid of tolerance and dependence liability (Auta et al., 2000; Costa et al., 2001). There are remarkably distinct features in the pharmacological profile of imidazenil (compared with alprazolam) and warrant consideration of imidazenil as a prospective drug to treat psychotic symptoms in schizophrenia and bipolar disorder patients with mania. In fact with alprazolam, sedation, amnesia, and tolerance and dependence liability appear with doses that are very close to those that cause anxiolytic and anticonvulsant actions (FIG. 1, Costa et al., 2001), whereas in the case of imidazenil, sedation, amnesia, tolerance, and dependence liability are virtually undetectable for a wide range of doses significantly higher than the doses used to elicit therapeutic responses (FIG. 1; Auta et al., 2000; Costa et al., 2001). Thus, imidazenil and its congeners appear to possess an ideal profile for selectively targeting a partial allosteric modulation of GABA-gated $Cl^-$ currents at $GABA_A$ receptor subtypes containing $\alpha_2$ and $\alpha_3$ receptors that are presumably altered in schizophrenia, leaving the $GABA_A$ receptor subtype containing $\alpha_1$ subunits occupied but silent and unavailable for occupation by putative endogenous benzodiazepine ligands.

Neocortical alterations, including decreased thickness, increased neuronal packing density, and neuropil hypoplasia associated with decreased expression density of apical dendritic spines and of presynaptic afferents ($GAD_{67}$ downregulation) impinging on postsynaptic spine densities have been reported in the postmortem brain of schizophrenia patients. These changes are similar to those detected in the cortex of HRM (FIG. 6). Since there is a downregulation of extracellular matrix reelin at postsynaptic densities in both schizophrenia and HRM, these cortical abnormalities may stem from a downregulation of reelin expression in HRM (Guidotti et al., 2000; Liu et al., 2001).

A robust reduction in the magnitude of the auditory startle reflex can be achieved by presenting a weak auditory (or visual or tactile) stimulus shortly before a loud stimulus eliciting startle. Prepulse inhibition of startle can be easily and reliably measured in humans (eyeblink reflex) as well as in rodents (whole body flinch). PPI is reduced in psychotic patients and their relatives and PPI deficit is correlated with thought disorder (Perry and Braff, 1995; Perry et al., 1999). Thus, PPI is an ideal objective animal model for exploration of the effects of new drugs for the treatment of psychotic symptoms (Swerdlow and Geyer, 1998). The theory that sensory gating deficit is a core characteristic of schizophrenia is consistent with clinical and experiential reports indicating that patients seem overwhelmed by sensory stimuli (from sources outside in the environment and from within their own bodies) and are seemingly unable to "gate in" relevant stimuli and "gate out" irrelevant or constantly present stimuli. The end result according to gating theory is thought disorder because of the "flooding" of higher order neuronal processing caused by excessive irrelevant stimulation.

We have recently reported that HRM, like schizophrenia patients, exhibit PPI deficit (Tueting et al., 1999). As in schizophrenia and other psychotic disorders (Kodsi and Swerdlow, 1995; Swerdlow and Geyer, 1998), PPI gating deficit in HRM can be attributed to a downregulation of GABAergic transmission. A common PPI deficit in HRM and schizophrenia is also consistent with the similarities in neocortical alterations in HRM and schizophrenia postmortem brain (FIG. 6), as well as with the role of reelin haploinsufficiency in the genesis of abnormal brain circuits related to behavior. We have therefore chosen to test the efficacy of imidazenil compared with alprazolam on PPI deficit using the HRM model.

a) Procedures:

The startle apparatus (SR-Lab, San Diego Instruments) consisted of a Plexiglas cylinder resting on a Plexiglas frame within a ventilated soundproof enclosure. Acoustic noise bursts were presented by. speaker 24 cm above the animal. and a piezo-electric device transduced any consequent motion (flinch) within the cylinder. Two stimulus trial types 1) 115 db startle stimulus only; or 2) 115 db stimulus preceded by a 75 or 80 db prepulse 100 msec before startle simulut onset were randomly presented with a mean intertrial interval of 20 sec. Stimuli were 30 msec in duration and were presented over a constant 65 db white noise background also present during a 5-min adaptation period.

Mean peak amplitude of the flinch response within a 200 msec window following presentation of the 115 db stimulus was calculated separately for each type of startle trial. Ratios reflecting the amount of inhibition due to the prepulse were calculated by dividing the difference between mean amplitude for startle and prepulse trials by the mean for the startle trials. PPI data are commonly presented in this ratio form to control for overall level of the startle reflex itself. Startle/intensity functions confirmed that the prepulse intensities selected failed to elicit startle when not paired with the startle stimulus, and that the 115 db startle stimulus was within the asymptotic range for startle response magnitude in both wild-type mice (WTM) and HRM.

Imidazenil or alprazolam was dissolved in DMSO, combined with oil, and injected subcutaneously at a volume of 0.1 ml/10 gm of body weight. The amount of DMSO was approximately 1% of total volume. Vehicle was prepared similarly and vehicle or drug was administered in counterbalanced order using a within-subject design. Following drug administration, the mouse was placed in an isolated cage for 10–15 min before being placed in the startle apparatus. Animals were tested between 11:00 hr and 15:00 hr.

b) Results

Figure 3:
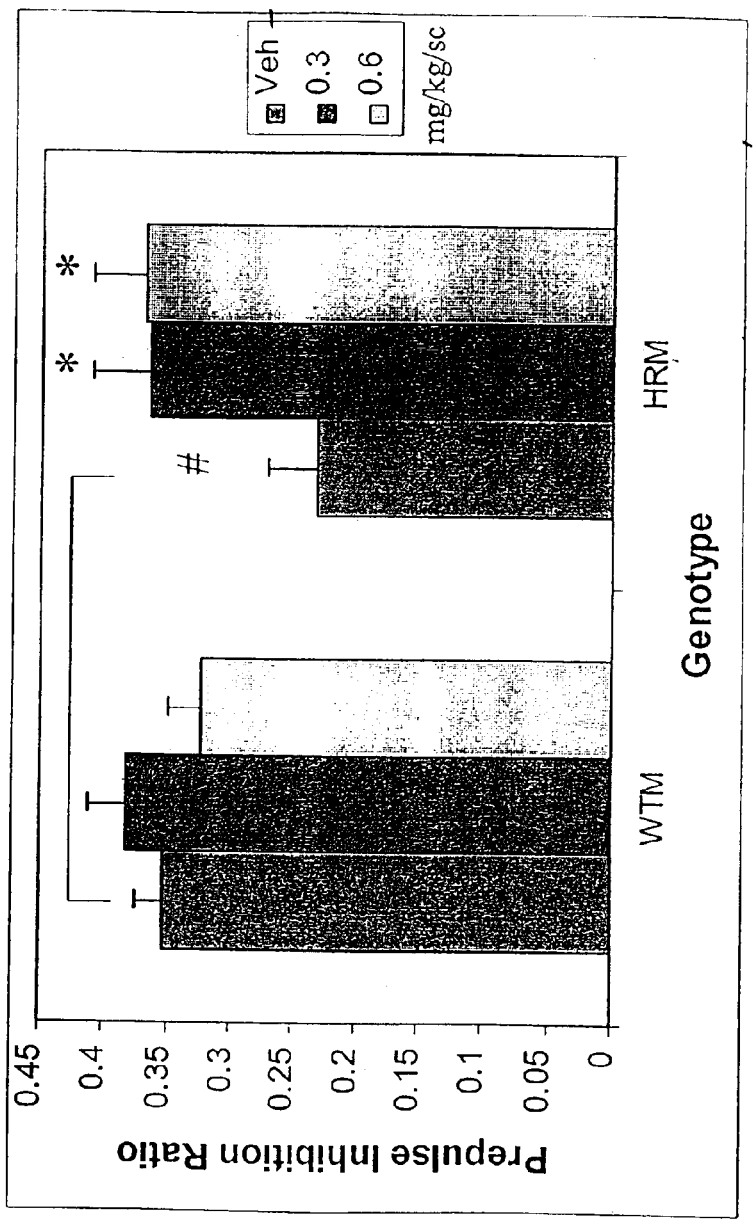
FIG. 3 is a Table showing the effect of imidazenil on prepulse inhibition of startle in wild type mice and heterozygous reeler mice.
Figure 4:
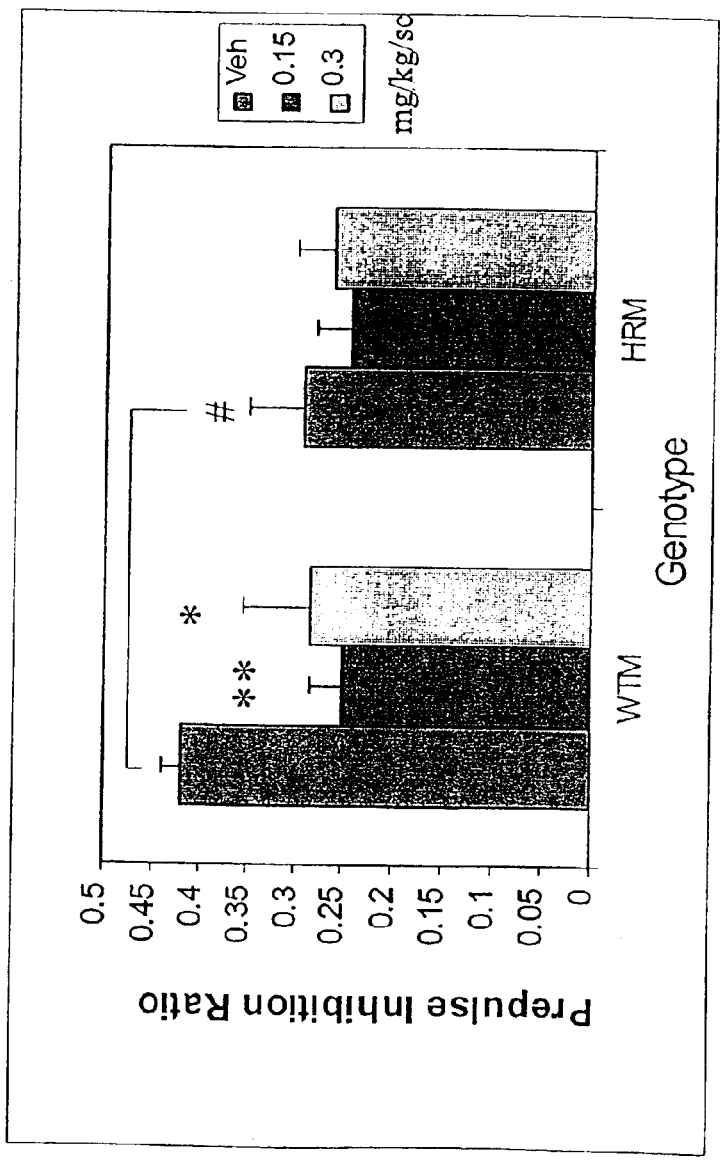
FIG. 4 is a Table showing the effect of alprazolam on prepulse inhibition of startle in wild type mice and heterozygous reeler mice.

FIGS. 3 and 4 show that imidazenil but not alprazolam corrected the auditory PPI deficit in HRM, largely by increasing PPI. Imidazenil's ability to increase PPI in HRM is obtained with doses of imidazenil that have no primary effects on the PPI of WTM and fail to change the overall startle level, indicating lack of sedative effects for doses of imidazenil (0.3, 0.6 mg/kg) that correct the deficit of PPI in HRM. In contrast to imidazenil, our reference classical BZ, alprazolam, which is sedative and amnestic at the same doses that presumably act on $GABA_A$ receptors that control sensory gating, decreased PPI in WTM and failed to revert the PPI deficit in HRM (FIG. 4). The ability of alprazolam to induce a PPI deficit in WTM is consistent with the results of human studies following classical benzodiazepine administration (Abduljawad et al., 1997; Rodriguez-Fornells et al., 1999; Schachinger et al., 1999), which also indicate that PPI is decreased following administration of classical sedative benzodiazepine ligands.

REFERENCES

Abduljawad K A F, Langely R W, Bradshaw C M, Szabadi E (1997) Effects of clonidine and diazepam on the acoustic startle response and on its inhibition by 'prepossess' in man. J Psychopharmacol 11:29–34.

Akbarian S, Kim J J, Potkin S G, Hagman J O, Tafazzoli A, Bunney Jr W E, Jones E G (1995) Gene expression for glutamic acid decarboxylase is reduced without loss of neurons in prefrontal cortex of schizophrenics. Arch Gen Psychiatry 562, 258–266.

Akbarian S, Kim J J, Potkin S G S Hetrick W P, Bunney Jr W E, Jones E G (1996) Maldistribution of interstitial neurons in prefrontal white matter of schizophrenics. Arch Gen Psychiatry 53, 178–187.

Auta J, Guidotti A, Costa E (2000) Imidazenil prevention of alprazolam-induced acquisition deficit in Patas monkey is devoid of tolerance. Proc Natl Acad Sci USA 91:2314–2319.

Barnard E A (2001) The molecular architecture of $GABA_A$ receptors. In Möhler H (ed) Handbook of Experimental Pharmacology Vol. 150: Pharmacology of GABA and Glycine Neurotransmission, Chapter 2, 79–94.

Benes F M (2000) Emerging principles of altered neuronal circuitry in schizophrenia. Brain Res Rev 31:251–269.

Benes F M, Vincent S L, Alsterberg Q Bird E D, San Giovanni J P (1992) Increased GABA receptor binding in supramolecular layers of schizophrenia cingulate cortex. J Neurosci 12, 924–929.

Bunney Jr W E, Bunney B'G (2000) Evidence for a compromised dorsolateral prefrontal cortical parallel circuit in schizophrenia. Brain Res Rev 31, 138–146.

Costa E, Guidotti A. (1996) Benzodiazepines on trial: a research strategy for their rehabilitation. TIPS 17:192–200.

Costa E, Auta J, Guidotti A (2001) Tolerance and dependence to ligands of the benzodiazepine recognition sites expressed by $GABA_A$ receptors. In Möhler H (ed) Handbook of Experimental Pharmacology Vol. 150: Pharmacology of GABA and Glycine Neurotransmission, Chapter 8, 227–250.

Guidotti A, Auta J, Davis J M, Dwivedi Y, Impagnatiello F, Pandey G N, Pesold C, Sharma R, Uzunov D P, Costa E (2000) Decrease in reelin and glutamic acid decarboxylase$_{67}$ (GAD67) expression in schizophrenia and bipolar disorder. A postmortem brain study. Arch Gen Psych 57:1061–1069.

Impagnatiello F, Guidotti A R, Pesold C, Dwivedi Y, Caruncho H, Pisu M G S Uzunov D P, Smalheiser N R, Davis J M, Pandey G N, Pappas G D, Tueting P, Sharma R P, Costa E (1998) A decrease of reelin expression as a putative vulnerability factor in schizophrenia. Proc Natl Acad Sci USA 95:15718–15723.

Kodsi M H, Swerdlow N R (1995) Ventral pallidal $GABA_A$ receptors regulate prepulse inhibition of acoustic startle: Brain Res 684:26–35.

Liu W S Pesold C, Rodriguez M A, Carboni G, Auta J, Lacor P, Larson J, Condie B G, Guidotti A, Costa E (2001) Downregulation of dendritic spine and glutamic acid decarboxylase 67 expression in the reelin haploinsuffcient heterozygous reeler mouse. Proc Natl Acad Sci USA 98:3479–3482.

Meldrum B J, Whiting D (2000) Anticonvulsants acting on the GABA system. In Möhler H (ed) Handbook of Experimental Pharmacology Vol. 150: Pharmacology of GABA and Glycine Neurotransmission, Chapter 2, pp 173–188.

Möhler H (2001) Functions of $GABA_A$ receptors: Pharmacology and pathophysiology. In Möhler H (ed) Handbook of Experimental Pharmacology Vol. 150: Pharmacology of GABA and Glycine Neurotransmission, Chapter 3, pp. 101–112.

Perry W, Braff D L (1994) Information-processing deficits and thought disorder in schizophrenia. Am J Psychiatry 151:363–367.

Perry W, Geyer M A, Braff D L (1999) Sensorimotor gating and thought disturbance measured in close temporal proximity in schizophrenia patients. Arch Gen Psychiatry 56:277–281.

Reynolds G P, Czudek C, Andrew H B (1990) Deficit and hemispheric asymmetry of GABA uptake sites in the hippocampus in schizophrenia. Biol Psychiatry 27:1038–1044.

Rodriguez-Formells A, Riba J, Gironell A, Kulisevksy J, Barbanoj M J (1998) Effects of alprazolam on the acoustic startle response in humans. Psychopharmacology 143:280285.

Schachinger H, Miller B U, Strobel W, Langewitz W, Ritz R (1999) Midazolam effects on prepulse inhibition of the acoustic blink reflex. Br. J Clin Pharmacol 47:421–426.

Sherman A D, Davidson A T, Baruah S, Hegwood T S, Waziri R (1991) Evidence of glutamatergic deficiency in schizophrenia. Neurosci Lett 121:77–80.

Simpson M D, Slater P, Deakin J F (1998) Gamma-aminobutyric acid uptake binding sites in frontal and temporal lobes in schizophrenia. Biol Psychiatry 44:423–427.

Swerdlow N R, Geyer M A (1998) Using an animal model of deficient sensorimotor gating to study the pathophysiology and new treatments of schizophrenia. Schiz Bull 24:285–301.

Tueting P, Costa E, Dwivedi Y, Guidotti A, Impagnatiello F, Manev R, Pesold C. (1999) The phenotypic characteristics of heterozygous reeler mouse. NeuroReport 10:1329–1334.

Volk D W Austin M C, Pierri S N, Sampson A R, Lewis D (2000) Decreased glutamic and decarboxylase messenger RNA expression in a subset of prefrontal cortical yaminobutyric acid neurons in subjects with schizophrenia. Arch Gen Psychiatry 57:237245.

Woo T U, Whitehead R E, Melchitzky D S, Lewis D A (1998) A subclass of prefrontal gammaamino butyric acid axon terminals are selectively altered in schizophrenia. Proc Natl Acad Sci USA 5341–5346.

What is claimed is:

1. A method of treating deficits in GAGAergic modulation in cortico-thalamic and cortico-hippocampal brain pathways in patients suffering from schizophrenia or bipolar disorder with mania which comprises administering to patients in need thereof a therapeutically effective amount of a compound of the formula:

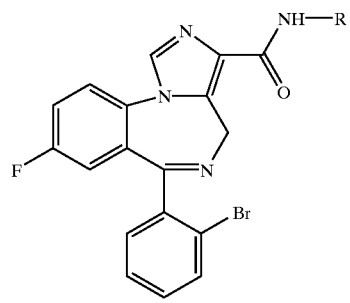

wherein R is selected from hydrogen, $CH_3CH_2$—, $CH_2=CHCH_2$—, $(CH_3)_2CH$—, $CH_3CH_2CH_2$— or

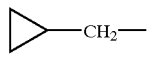

or a pharmaceutically acceptable salt thereof.

2. A method as claimed in claim 1 wherein R is hydrogen.

3. A method as claimed in claim 1 wherein the compound is administered in the form of capsules or pills.

4. A method as claimed in claim 1 wherein the compound is administered at a dosage of from 1 to 10 μg/kg body weight/day.

5. A method of treating prepulse inhibition deficit in patients suffering from schizophrenia or bipolar disorder with mania which comprises administering to patients in need thereof a therapeutically effective amount of a compound of the formula:

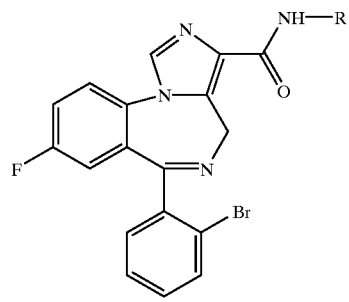

wherein R is selected from hydrogen, $CH_3CH_2$—, $CH_2=CHCH_2$—, $(CH_3)_2CH$—, $CH_3CH_2CH_2$— or

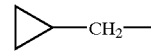

or a pharmaceutically acceptable salt thereof.

* * * * *